(12) United States Patent
White et al.

(10) Patent No.: US 8,309,746 B2
(45) Date of Patent: Nov. 13, 2012

(54) METHODS FOR PREPARING 17-ALKYNYL-7-HYDROXY STEROIDS AND RELATED COMPOUNDS

(75) Inventors: Steven K. White, San Diego, CA (US); Yu Ge, San Diego, CA (US); Yujin Huang, San Diego, CA (US)

(73) Assignee: Harbor Therapeutics, Inc, San Diego, CA (US)

( * ) Notice: Subject to any disclaimer, the term of this patent is extended or adjusted under 35 U.S.C. 154(b) by 515 days.

(21) Appl. No.: 12/479,626

(22) Filed: Jun. 5, 2009

(65) Prior Publication Data

US 2009/0326251 A1    Dec. 31, 2009

Related U.S. Application Data

(60) Provisional application No. 61/059,658, filed on Jun. 6, 2008.

(51) Int. Cl.
*C07J 1/00* (2006.01)
(52) U.S. Cl. ...................................... 552/615
(58) Field of Classification Search ................ 552/615
See application file for complete search history.

(56) References Cited

U.S. PATENT DOCUMENTS

| | | | |
|---|---|---|---|
| 4,898,694 | A | 2/1990 | Schwartz et al. |
| 5,476,932 | A | 12/1995 | Brinckman et al. |
| 5,717,103 | A | 2/1998 | Denis et al. |
| 5,859,000 | A | 1/1999 | Dowell et al. |
| 5,922,701 | A | 7/1999 | Araneo |
| 6,403,567 | B1 | 6/2002 | Zablocki et al. |
| 6,667,299 | B1 | 12/2003 | Ahlem et al. |
| 6,693,205 | B2 | 2/2004 | Justice |
| 7,365,188 | B2 | 4/2008 | Roberts et al. |
| 7,462,640 | B2 | 12/2008 | Merce Vidal et al. |
| 7,524,835 | B2 | 4/2009 | Frincke |
| 7,691,835 | B2 | 4/2010 | Frincke |
| 7,696,189 | B1 | 4/2010 | Frincke |
| 7,776,845 | B2 | 8/2010 | Frincke |
| 7,863,261 | B2 | 1/2011 | Frincke |
| 7,956,179 | B2 | 6/2011 | Zablocki et al. |
| 8,097,643 | B2 | 1/2012 | Merce Vidal et al. |
| 2003/0060425 | A1 | 3/2003 | Ahlem et al. |
| 2003/0083231 | A1 | 5/2003 | Ahlem et al. |
| 2004/0087562 | A1* | 5/2004 | Marie Wuts ................ 514/173 |
| 2005/0075321 | A1 | 4/2005 | Ahlem et al. |
| 2006/0079492 | A1 | 4/2006 | Ahlem et al. |
| 2006/0088473 | A1 | 4/2006 | Dowding et al. |
| 2007/0077201 | A1 | 4/2007 | Reading et al. |
| 2007/0129282 | A1 | 6/2007 | Ahlem et al. |
| 2008/0015174 | A1 | 1/2008 | Reading et al. |
| 2008/0146532 | A1 | 6/2008 | Flores-Riveros et al. |
| 2008/0153792 | A1 | 6/2008 | Frincke et al. |
| 2008/0153797 | A1 | 6/2008 | Frincke et al. |
| 2008/0221074 | A1 | 9/2008 | Frincke et al. |
| 2009/0326251 | A1 | 12/2009 | White et al. |
| 2010/0075937 | A1 | 3/2010 | Flores-Riveros et al. |

FOREIGN PATENT DOCUMENTS

| | | |
|---|---|---|
| EP | 0 624 162 B1 | 9/1998 |
| EP | 0 700 291 B1 | 9/1998 |
| FR | 2835839 * | 8/2003 |
| WO | WO 01/30802 | 5/2001 |
| WO | WO 2008/039566 | 4/2008 |

OTHER PUBLICATIONS

Negi et al, "An approach towards the development of progesterone antagonists: Synthesis of 7alpha/beta-aryl androstene derivatives", Steroids, vol. 60, pp. 470-472, 1995.*
Fieser et al., "Preparation of Ethylenethioketals", J. of the American Chem. Soc., vol. 76, pp. 1945-1947, 1954.*
Pearson et al., "A new method for the oxidation of alkenes to enones. An efficient synthesis of 5-en-7-oxo steroids", J. Chem. Soc. Perkin Trans 1, pp. 267-273, 1985.*
English translation of FR2835839 filed Aug. 2003.*
International Search Report PCT/US09/46477, 2009.
Written Opinion ISA PCT/US09/46477, 2009.
*Ex parte Buysch*, Appeal No. 1994-0210, 1996 WL 1796251 (non-precedential).
*Ex parte Coates*, Appeal No. 1996-2321, 2000 WL 33201011 (non-precedential).
*Ex parte Humberto*, Appeal No. 1994-2062, 1994 WL 1687072 (non-precedential).
*Ex parte Schwideman*, Appeal No. 2002-2283, 2003 WL 25283910 (non-precedential).
*Ex parte Shiragami*, Appeal No. 1997-0481, 2002 WL 43702 (non-precedential).
*Ex parte Sowerby*, Appeal No. 1994-4429, 1994 WL 1687166 (non-precedential).

* cited by examiner

*Primary Examiner* — Barbara P Badio
(74) *Attorney, Agent, or Firm* — Angelo Castellino

(57) ABSTRACT

The invention relates to processes for preparing 17-alkynyl-7-hydroxy-steroids, such as 17-Ethynyl-10R,13S-dimethyl 2,3,4,7,8R,9S, 10,11,12,13,14S,15,16,17-hexadecahydro-1H-cyclopenta[a]phenanthrene-3R, 7R,17S-triol (also referred to as 17α-ethynyl-androst-5-ene-3β,7β,17β-triol), that are essentially free of process impurities having binding activity at nuclear estrogen receptors.

12 Claims, No Drawings

US 8,309,746 B2

METHODS FOR PREPARING 17-ALKYNYL-7-HYDROXY STEROIDS AND RELATED COMPOUNDS

CROSS-REFERENCE TO RELATED APPLICATIONS

This nonprovisional U.S. patent application claims priority from pending U.S. provisional application Ser. No. 61/059,658 filed Jun. 6, 2008, which is incorporated herein by reference in its entirety.

FIELD OF THE INVENTION

Invention embodiments relate to methods for preparing 17-Ethynyl-10R,13S-dimethyl 2,3,4,7,8R,9S, 10,11,12,13,14S,15,16,17-hexadecahydro-1H-cyclopenta[a]phenanthrene-3R,7R,17S-triol and other pharmaceutically active compounds related thereto, that are essentially free of reaction steroid impurities having undesired binding activity at sex steroid receptors.

BACKGROUND OF THE INVENTION

17-Ethynyl-10R,13S-dimethyl 2,3,4,7,8R,9S, 10,11,12,13,14S,15,16,17-hexadecahydro-1H-cyclopenta[a]phenanthrene-3R,7R,17S-triol (also referred to herein as 17α-ethynyl-androst-5-ene-3β,7β,17β-triol or Compound 1) is effective in treating conditions that are attributable to chronic non-productive inflammation. In contrast to other anti-inflammatory steroids, Compound 1 has been found to be essentially free of binding activity at nuclear sex steroid receptors, activity which can contribute to unwanted side effects from such compounds. Steroid synthetic intermediates, by-products, side products or other such impurities that can affect or modulate sex steroid receptor activity(ies) and may be present in preparations of Compound 1 are undesirable, since they contribute to side effects. Thus, methods for preparing Compound 1 and analogs and derivatives thereof that avoid production of impurities, such as synthetic intermediates, steroid side-products or byproducts that affect or modulate nuclear sex steroid activity(ies) are useful.

SUMMARY OF THE INVENTION

Reaction sequences to provide 17α-alkynyl-androst-5-ene-3β,7β,17β-triol have unexpectedly been found to produce material containing undesired steroid impurity(ies) that impart sex steroid receptor activity(ies) that otherwise would not be present to the material. These impurities adversely affect the pharmaceutical acceptability of the 17α-alkynyl-androst-5-ene-3β,7β,17β-triol. The presence of these impurities in preparations of 17α-alkynyl-androst-5-ene-3β,7β,17β-triol has not been described and their presence adds additional cost to remove or reduce their presence to a level at which the sex steroid activity(ies) would not be present. The reaction sequences disclosed herein avoid production of the undesired steroid impurity(ies) and thus avoid the need for purification of the 17α-alkynyl-androst-5-ene-3β,7β,17β-triol so produced to effect removal or reduction in level of the impurity(ies).

One embodiment of the invention provides a reaction sequence for introducing an alkynyl group at position 17 and an oxygen functionality at position 7 to an androst-5-ene having an oxygen linked group at position 3 and a ketone at position 17 such that a side-product lacking a oxygen substituent at C-7, and thus having undesired binding activity at sex steroid receptors, is precluded.

Another embodiment of the invention provides a reaction sequence for introducing an ethynyl group at position 17 and a hydroxy group at position 7 to dehydroepiandrosterone (also referred herein as DHEA or 3β-hydroxy-androst-5-ene-17-one) such that a preparation of Compound 1 is formed that is essentially free of binding activity at sex steroid receptors.

In another embodiment of the invention provides for a reaction sequence that uses DHEA as starting material to obtain a preparation containing Compound 1 that is essentially free of the estrogenic compound 17α-ethynyl-androst-5-ene-3β,17β-diol or its potential precursor 17α-ethynyl-3β-acetoxy-androst-5-ene-17β-ol.

In one embodiment of the invention the reaction sequence comprises a prior step of oxidizing an appropriately protected androst-5-ene having a first and second oxygen linked group at positions 3 and 17 such that a third oxygen linked group is introduced at position 7 and a subsequent step of reacting an intermediate wherein the second oxygen linked group at position 17 is =O with an anion derived from an alkyne.

In another embodiment of the invention the reaction sequence comprises a prior step of oxidizing DHEA, appropriately protected, to introduce a third oxygen linked group at position 7 and a subsequent step of reacting of an intermediate having the substituent =O at position 17 with an acetylene anion, optionally protected.

In another embodiment of the invention the reaction sequence comprises the step of reacting androst-5-en-17-one-3β,7β-diol, appropriately protected, with an anion derived from an alkyne.

DETAILED DESCRIPTION

Definitions As used herein and unless otherwise stated or implied by context, terms that are defined herein have the meanings that are specified. The descriptions of embodiments and examples that are described illustrate the invention and they are not intended to limit it in any way. Unless otherwise contraindicated or implied, e.g., by including mutually exclusive elements or options, in these descriptions and throughout this specification, the terms "a" and "an" mean one or more and the term "or" means and/or.

"Alkyl" as used here refers to linked normal, secondary, tertiary or cyclic carbon atoms, i.e., linear, branched, cyclic or any combination thereof. Alkyl groups or moieties, as used herein, may be saturated, or unsaturated, i.e., the moiety may comprise one, two, three or more independently selected double bonds or triple bonds. Unsaturated alkyl moieties include moieties as described below for alkenyl, alkynyl, cycloalkyl, and aryl moieties. The number of carbon atoms in an alkyl moiety is 1-20, preferably 1 to 8. $C_{1-8}$ alkyl or C1-8 alkyl means an alkyl moiety containing 1, 2, 3, 4, 5, 6, 7 or 8 carbon atoms and $C_{1-6}$ alkyl or C1-8 alkyl means an alkyl moiety containing 1, 2, 3, 4, 5 or 6 carbon atoms. When an alkyl moiety is specified, species may include methyl, ethyl, 1-propyl(n-propyl), 2-propyl(iso-propyl, —CH(CH$_3$)$_2$), 1-butyl(n-butyl), 2-methyl-1-propyl(iso-butyl, —CH$_2$CH(CH$_3$)$_2$), 2-butyl(sec-butyl, —CH(CH$_3$)CH$_2$CH$_3$), 2-methyl-2-propyl (t-butyl, —C(CH$_3$)$_3$), 1-pentyl(n-pentyl), 2-pentyl (—CH(CH$_3$)CH$_2$CH$_2$CH$_3$), 3-pentyl (—CH(CH$_2$CH$_3$)$_2$) and 2-methyl-2-butyl (—C(CH$_3$)$_2$CH$_2$CH$_3$).

"Cycloalkyl" as used here refers to a monocyclic, bicyclic or tricyclic ring system composed of only carbon atoms. The number of carbon atoms in an cycloalkyl group or moiety can vary and typically is 3 to about 20, e.g., preferably 3-8. $C_{3-8}$ alkyl or C3-C8 alkyl means an cycloalkyl moiety containing 3, 4, 5, 6, 7 or 8 carbon atoms and $C_{3-6}$ alkyl or C3-C6 means an cycloalkyl moiety containing 3, 4, 5 or 6 carbon atoms. Preferred cycloalkyl substituents are cyclopropyl, cyclopentyl, cyclohexyl, cycloheptyl and adamantyl. Cycloalkyl substituents having a double bond within the cyclic ring system are sometimes referred to as cycloalkenyl substituents.

"Alkenyl" as used here means a moiety or group that comprises one or more double bonds (—CH=CH—), e.g., 1, 2, 3, 4, 5, 6 or more, typically 1, 2 or 3 and can include an aryl moiety such as benzene, and additionally comprises linked normal, secondary, tertiary or cyclic carbon atoms, i.e., linear, branched, cyclic or any combination thereof unless the alkenyl moiety is vinyl (—CH=CH$_2$). An alkenyl moiety with multiple double bonds may have the double bonds arranged contiguously (i.e., a 1,3 butadienyl moiety) or non-contiguously with one or more intervening saturated carbon atoms or a combination thereof, provided that a cyclic, contiguous arrangement of double bonds do not form a cyclically conjugated system of 4n+2 electrons (i.e., aromatic). The number of carbon atoms in an alkenyl moiety can is 2-20, preferably 2-8. $C_{2-8}$ alkenyl or C2-8 alkenyl means an alkenyl moiety containing 2, 3, 4, 5, 6, 7 or 8 carbon atoms and $C_{2-6}$ alkenyl or C2-6 alkenyl means an alkenyl moiety containing 2, 3, 4, 5 or 6 carbon atoms. When an alkenyl moiety is specified, species include, e.g., any of the alkyl moieties described above that has one or more double bonds such as methylene (=CH$_2$), methylmethylene (=CH—CH$_3$), ethylmethylene (=CH—CH$_2$—CH$_3$), propylmethylenes (=CH—CH$_2$—CH$_2$—CH$_3$), vinyl (—CH=CH$_2$), allyl (—CH=CHCH$_3$), 1-methylvinyl, butenyl, iso-butenyl, 3-methyl-2-butenyl or 1-pentenyl.

"Alkynyl" as used herein refers to linked normal, secondary, tertiary or cyclic carbon atoms where one or more triple bonds (—C≡C—) are present, typically 1, 2 or 3, usually 1, optionally comprising 1, 2, 3, 4, 5, 6 or more double bonds, with the remaining bonds (if present) being single bonds and comprising linked normal, secondary, tertiary or cyclic carbon atoms, i.e., linear, branched, cyclic or any combination thereof, unless the alkynyl moiety is ethynyl. The number of carbon atoms in an alkynyl group or moiety is 2 to 20, preferably 2-8. $C_{2-8}$ alkynyl or C2-8 alkynyl means an alkynyl moiety containing 2, 3, 4, 5, 6, 7 or 8 carbon atoms. When an alkynyl substituent is specified, preferred species include, —C≡CH, —C≡CCH$_3$, —C≡CCH$_2$CH$_3$, —C≡CC$_3$H$_7$ and —C≡CCH$_2$C$_3$H$_7$. Particularly preferred species are ethynyl, propynyl and 1-butynyl with ethynyl especially preferred.

"Aryl" as used herein refers to an aromatic ring system or a fused ring system with no ring heteroatoms comprising 1, 2, 3 or 4 to 6 rings, typically 1 to 3 rings; wherein the rings are composed of only carbon atoms; and refers to a cyclically conjugated system of 4n+2 electrons (Hückel rule), typically 6, 10 or 14 electrons some of which may additionally participate in exocyclic conjugation (cross-conjugated). When an aryl group is specified, species may include phenyl, biphenyl, naphthyl, phenanthryl and quinone.

"Heteroaryl" as used here refers means an aryl ring system wherein one or more, typically 1, 2 or 3, but not all of the carbon atoms comprising the aryl ring system are replaced by a heteroatom which is an atom other than carbon, including, N, O, S, Se, B, Si, P, typically, oxygen (—O—), nitrogen (—NX—) or sulfur (—S—) where X is —H, a protecting group or $C_{1-6}$ optionally substituted alkyl, wherein the heteroatom participates in the conjugated system either through pi-bonding with an adjacent atom in the ring system or through a lone pair of electrons on the heteroatom and may be optionally substituted on one or more carbons or heteroatoms, or a combination of both, comprising the heterocycle in a manner which retains the cyclically conjugated system.

"Protecting group" as used here means a moiety that prevents or reduces the atom or functional group to which it is linked from participating in unwanted reactions. For example, for —OR$^{PR}$, R$^{PR}$ is a protecting group for the oxygen atom found in a hydroxyl, while for =O the protecting group is a ketal or thioketal wherein the divalent oxygen is replaced, for example, by —X—(CH$_2$)$_n$—Y—, wherein X and Y independently are S and O and n is 2 to 3, to form a spiro ring system or an oxime wherein the divalent oxygen is replaced by =N—OR, wherein R is —H, alkyl or aryl. For —C(O)—OR$^{PR}$, R$^{PR}$ is a carbonyloxy protecting group, for —SR$^{PR}$, R$^{PR}$ is a protecting group for sulfur in thiols for instance, and for —NHR$^{PR}$ or —N(R$^{PR}$)$_2$—, R$^{PR}$ is a nitrogen atom protecting group for primary or secondary amines. The protecting groups for sulfur or nitrogen or monovalent oxygen atoms are usually used to prevent unwanted reactions with electrophilic compounds. The protecting groups for divalent oxygen atoms (i.e. =O) are usually used to prevent unwanted reactions with nucleophilic compounds.

"Optionally substituted alkyl", "optionally substituted alkenyl", "optionally substituted alkynyl", "optionally substituted heterocycle", "optionally substituted aryl", "optionally substituted heteroaryl" and the like mean an alkyl, alkenyl, alkynyl, aryl, heteroaryl or other group or moiety as defined or disclosed herein that has a substituent(s) that optionally replaces a hydrogen atom(s). Such substituents are as described above. For a phenyl moiety (-Ph), the arrangement of any two substituents present on the aromatic ring can be ortho (o), meta (m), or para (p) to each other. Preferred optionally substituted moieties are —CF$_3$, —CH$_2$OH, —C≡C—Cl and -Ph-F.

"O-linked group", O-linked substituent and like terms as used herein refers to a group or substituent that is attached to a moiety directly though an oxygen atom of the group or substituent. An O-linked group may be monovalent including groups such as —OH, acetoxy, i.e., —O—C(O)—CH$_3$, acyloxy, i.e., —O—C(O)—R wherein R is —H, optionally substituted alkyl, optionally substituted cycloalkyl, optionally substituted alkenyl, optionally substituted alkynyl, optionally substituted aryl, optionally substituted heteroaryl or optionally substituted heterocycle, aryloxy (Aryl-O—), phenoxy (Ph-O—), heteroaryloxy(Heteroaryl-O—), silyloxy, i.e. R$_3$SiO—wherein R independently are alkyl or aryl, optionally substituted or —OR$^{PR}$ wherein R$^{PR}$ is a protecting group as previously defined or may be divalent, i.e. =O.

The term "preparation of Compound 1" refers to material prepared according to any one of the synthetic schemes specifically or generically described and includes Compound 1 wherein Compound 1 is found as the major component on a mass basis and process impurities, present either in Compound when initially isolated as a solid or after recrystallization and-or purification of the solid.

The term "binding activity" refers to the ability of a specified compound, a preparation comprising Compound 1 or impurity (or impurities) in a preparation of Compound 1 to bind to or associate with a receptor, typically a sex steroid receptor such as an androgen receptor or an estrogen receptor to effect or modulate the receptor's biological activity. Binding is usually measured in assays as the capacity of a compound, usually an impurity in a preparation comprising Compound 1, to displace a physiologically relevant ligand of a receptor (i.e., reference ligand) that is bound to that receptor in a competition assay. The reference ligand is typically a natural ligand of the receptor or an agonist of the receptor that has been labeled with a radioactive or spectroscopic probe whose presence may be queried by scintillation counting or by a spectroscopic method such as fluorescence emission or fluorescence polarization.

The radioactive probe is typically $^3H$ and/or $^{14}C$, where radioactive atom(s) have replaced one or more of atoms of the ligand at positions where loss of the radiolabel would not occur to an extent under conditions of the assay that would complicate or confound interpretation of the assay results. The spectroscopic probe is typically a fluorophore that is attached to a reference ligand at a position that provides a labeled reference ligand that has a $K_d$ in the range of 0.1-100 nM at positions and will not lose the fluorescent label to an extent under conditions of the assay that would complicate or confound interpretation of the assay results. The binding activity of the specified compound or a preparation of Compound 1 is typically expressed by $K_i$, wherein $K_i$ is determined from the concentration the specified compound or preparation to displace the labeled reference ligand to the receptor by 50% and the Kd of the labeled reference ligand.

"Sex steroid receptor" refers to nuclear receptors normally associated with affecting the growth or function of the reproductive organs and the development of secondary sex characteristics and includes androgen receptor, estrogen receptor-α(ERα), estrogen receptor-β (ERβ) and progesterone receptor.

"Essentially free" as used herein refers to a property of or an impurity in a preparation of Compound 1 as not being present or measurable in an amount that would adversely affect or detract from the desired pharmacological activity of Compound 1. For example, the term "essentially free of sex steroid receptor binding activity" refers to the absence of receptor binding activity for a preparation of Compound 1 to nuclear sex steroid receptors as defined by values of $K_i$>10 µM for binding to those receptors, as determined using standard receptor binding assay conditions, and is irrespective of the identity of the impurity that may be present in the preparation that would give rise to the sex receptor binding activity. Likewise, essentially free of estrogen receptor binding activity estrogen receptors refers to the absence of receptor binding activity for a preparation of Compound 1 to nuclear estrogen receptors ERα and ERβ as defined by values of $K_i$>10 µM for binding to those receptors, as determined using standard receptor binding assay conditions, and is irrespective of the identity of the impurity that may be present in the preparation that would give rise to the estrogen receptor binding activity. When the term "essentially free" is used to describe the amount of an impurity present in a preparation of Compound 1, the term means the impurity is not present in an amount that would adversely affect the pharmacological activity of Compound 1 for its intended use by contributing to side effects normally attributable to activation of nuclear estrogen receptor that are due to binding activity of the impurity at these receptors. The impurity (e.g., 17α-ethynyl-androst-5-ene-3β,17β-diol) may directly affect the pharmacological activity of Compound 1 by binding or modulating the estrogen receptor or may indirectly affect the pharmacological activity of Compound 1 by its conversion in a subject being treated with a composition comprising a preparation of Compound 1 by hydrolysis (either spontaneously or enzymatically) to a compound that does affect or modulate the estrogen receptor (e.g., 17α-ethynyl-3β-acetoxy-androst-5-ene-17β-ol converting to 17α-ethynyl-androst-5-ene-3β17β-ol).

The terms "impurity" or "process impurity" as used herein refers to a component in a preparation of Compound 1 that is a steroid byproduct, side-product or a degradation product formed during synthesis of Compound 1 and represents a minority contribution to the overall mass of the preparation, typically less than about 2%.

"Formulation" or "pharmaceutically acceptable formulation" as used herein refers to a composition comprising a preparation of Compound 1, and one or more pharmaceutically acceptable excipients.

The inventions described herein provide for methods of preparing 17-alkynyl steroids having oxygen substituents at positions 3, 7 and 17 that are essentially free of impurities that have undesired binding activity at sex steroid receptors. Such 17-alkynyl steroids so prepared are essentially free of one or more impurities that are characterized by lacking the oxygen substituent at C7, which are responsible for the undesired binding activity.

The present methods were developed in response to unexpected estrogenic effects seen with Compound 1. Compound 1 was prepared by the route comprising the following steps referred to as Process A:

(1) Contacting a suitably protected acetylene anion with suitably protected dehydroepiandrosterone to introduce the ethynyl group at position 17α by addition of the acetylene anion to the =O functional group at position 17;

(2) Contacting suitably protected 17α-ethynyl-androst-5-ene-3β,17α-diol with an oxidizing agent to introduce the =O functional group at position 7; and (3) Contacting suitably protected 17α-ethynyl-androst-5-en-7-one-3β,17α-diol with a reducing agent to directly convert the =O functional group at position 7 to β-hydroxyl.

An embodiment of Process A is given in Scheme I (herein referred to as Process A, Route 1). Compound 1 so produced was unexpectedly found to have estrogenic effects. Impurity profiling of Compound 1 prepared by this route showed the presence of 17α-ethynyl-androst-5-ene-3β,17β-diol, which has the same structure as Compound 1 except the β-hydroxy group at position 7 is absent. Receptor binding studies showed that 17α-ethynyl-androst-5-ene-3β,17β-diol had significant binding activity at the estrogen receptors ERα and ERβ, whereas Compound 1 essentially free of this impurity possessed no activity at these receptors when tested to 10 µM. Based upon this undesired sex steroid activity, a new process, referred to as Process B, was developed that circumvented production of the estrogenic side product 17α-ethynyl-androst-5-ene-3β,17β-diol.

Process B comprises the following steps.

(a) Contacting a suitably protected dehydroepiandrosterone with an oxidizing agent to directly introduce the =O functional group at position 7;

(b) Contacting a suitably protected androst-5-en-7,17-di-one-3β-ol with a reducing agent to convert the =O functional group at position 7 to β-hydroxyl;

(c) Contacting a suitably protected acetylene anion with suitably protected androst-5-en-17-one-3β,7β-diol to introduce the ethynyl group at position 17α by addition of the acetylene anion to the =O functional group at position 17.

Procedures to effect step (a) include microbial oxidation as described in Wuts, P. G. M. "A chemobiological synthesis of eplerenone" *Synlett* (3): 418-422 (2008); oxidation with oxochromium based reagents [e.g., see Koutsourea, et al., "Synthetic approaches to the synthesis of a cytostatic steroidal B-D bilactam" *Steroids* 68: 569-666 (2003) and Condom, et al., "Preparation of steroid-antigens through positions of the steroid not bearing functional groups" *Steroids* 23: 483-498 (1974)], peroxide assisted allylic oxidation [e.g., see Marwah, P., et al. "An economical and green approach for the oxidation of olefins to eneones" *Green Chem.* 6: 570-577 (2004) and Marwah, P., et al., "Ergosteroids IV: synthesis and biological activity of steroid glucuronosides, ethers and alkylcarbonates" *Steroids* 66: 581-595 (2001)], oxidation with N-hydroxysuccimimide/AIBN [e.g., see Lardy, et al. "Ergosteroids II: Biologically active metabolites and synthesis derivatives of dehydroepiandrosterone" *Steroids* 63:158-165 (1998)].

For step (a), a suitably protected dehydroepiandrosterone has the 3β-hydroxyl and ═O functional groups protected with protecting groups typically employed for hydroxyl and ketone given in Greene, T. W. "Protecting groups in organic synthesis" Academic Press, 1981. The hydroxy protecting group should be suitable for conditions required to (1) protect the ═O functional group at position 17, if not already present, or (1') does not require conditions to introduce that adversely effect a ketone protecting group previously introduced to position 17, and (2) introduce directly the ═O functional group at position 7. Preferred hydroxy protecting groups are also suitable for conditions required to (3) reduce the ═O functional group to be introduced at position 7 with sufficient selectivity to provide 7β-hydroxy as the predominant isomer and (4) removed under conditions where an allyl alcohol that is formed by the ═O functional group reduction has sufficient stability. Hydroxy protecting groups meetings conditions (1)-(4) include ester, usually aryl ester or $C_{1-6}$ alkyl ester, when the protecting group for the ═O functional group at position 17 is ketal and the reducing agent to be used is a borohydride based reducing agent. Use of a stronger hydride reducing agent would require a hindered ester or substituted methyl ether as the hydroxy protecting group to prevent premature loss of the hydroxy protecting group. Preferred ═O protecting groups are ketal, such as dimethyl ketal, diethyl ketal or the spiro ketal prepared from ethylene glycol. A preferred suitably protected dehydroepiandrosterone is the ethylene ketal of 3β-acetoxy-androst-5-en-17-one.

Procedures to effect step (b) include reduction with metal hydride based reagents such as the borohydride based reagents that include $Zn(BH_4)_2$, $NaBH_4$, optionally with a transition metal salt such as $CeCl_3$, $NiCl_2$, $CoCl_2$ or $CUCl_2$, L-Selectride (lithium tri-sec-butylborohydride) or N-Selectride (sodium tri-sec-butylborohydride). Lithium aluminum hydride based or sodium aluminum hydride reagents may also be used although selectivity may suffer due to the reducing strength of such reagents. This may be ameliorated by using lithium aluminum hydride based reagents having alkoxy ligands to aluminum to reduce reactivity. Such reagents have the general formula $LiAl—H_n(OR)_{4-n}$, where n=1, 2, 3, R is C1-6 alkyl and include LTMA (lithium triethoxyaluminum hydride LTEAH (lithium triethoxyaluminum hydride), RED-AL (Sodium bis(2-methoxyethoxy)aluminium hydride). Reduction using borohydride based reagents may be conducted in alcohol solvents whereas reductions with aluminium hydride based reagents require an ether solvent such as THF. Selectivity may be improved, particularly for the aluminum hydride reagents, by conducting the reaction at temperature of between 0° C. to −78° C. with lower temperatures being more suitable for the aluminum hydride reagents.

Procedures to effect step (c) include in situ preparation of an acetylene anion followed by contact of the acetylide so formed with a suitably protected androst-5-en-17-one-3β,7β,17β-triol. The acetylide may be prepared by contacting acetylene with an amide anion (e.g., $NaNH_2$) in a hydrocarbon solvent such as benzene, toluene or xylene, as for example in U.S. Pat. No. 2,251,939, with sodium or potassium metal in liquid ammonia, as for example in U.S. Pat. No. 2,267,257, or by contacting a mono-silyl protected acetylene such as trimethylsilyl acetylene with an organolithium reagent. Suitable organolithium reagents include commercially available n-butyl lithium, sec-butyl lithium, methyl lithium, t-butyl lithium or phenyl lithium or can be prepared by reaction of an alkyl or aryl bromide with metallic lithium in an inert solvent such as diethyl ether or tetrahydrofuran. The acetylide so prepared is then contacted with a suitably protected androst-5-en-17-one-3β,17β-diol.

For step (c), a suitably protected androst-5-en-17-one-3β,7β-diol will have hydroxyl protecting groups that are typically used in carbanion chemistry and may be removed under conditions that are compatible with the presence of a terminal alkyne and an allylic alcohol and include protecting groups that are removed under neutral or mildly acidic conditions, typically between pH 3-7 and can be introduced under conditions compatible with an allylic alcohol. Preferred protecting groups are silyl ethers of the formula $(R^1)_3SiO$— wherein $R^1$ independently are aryl or C1-6 alkyl and include trimethylsilyl, triethylsilyl, t-butyldimethylsilyl, isopropyldimethylsilyl, t-butyldiphenylsilyl, methyldiisopropylsilyl, methyl-t-butylsilyl, tribenzylsilyl and triphenylsilyl ether. Preferred silyl ethers are trimethylsilyl ether and t-butyldimethylsilyl ether. Some substituted methyl ethers may be used and include 2-(trimethylsilyl)-ethoxymethyl ether (SEM ether), tetrahydropyranyl ether (THP ether), tetrahydrothiopyranyl ether, 4-methoxy-tetrahydropyranyl ether, 4-methoxytetrahydrothiopyranyl ether, tetrahydrofuranyl ether and tetrahydrothiofuranyl ether. Some substituted ethyl ethers that may be used as hydroxy protecting groups and include 1-ethoxyethyl ether and t-butyl ether. Preferred hydroxy protecting groups have lower steric demands, such as trimethylsilyl ether and allow for simultaneous protection of the 3β- and 7β-hydroxy groups.

Other procedures to effect step (c) include contacting a suitably protected androst-5-en-17-one-3β,7β-diol with sodium acetylide, lithium acetylide (as its ethylene diamine complex), ethynyl magnesium halide (e.g., chloride or bromide) or ethynyl zinc halide, as for example in U.S. Pat. No. 2,243,887, in diethylether or other ether solvents such as tetrahydrofuran, 1,2-dimethoxyethane, 2-methoxyethylether and the like.

One embodiment of Process B uses 3β-acetoxy-androst-5-en-7-one-17,17-ethylenedioxy as the suitably protected androst-5-en-7,17-dione-3β-ol (see Scheme II; herein referred to as Process B, Route 1).

Another embodiment of Process B uses 3β-acetoxy-androst-5-en-7-on-17-oxime as the suitably protected androst-5-en-7,17-dione-3β-ol (see Scheme III; herein referred to as Process B, Route 2)).

The following examples and schemes further illustrate the invention and they are not intended to limit it in any way.

Scheme I. Process A, Route 1

Step 1

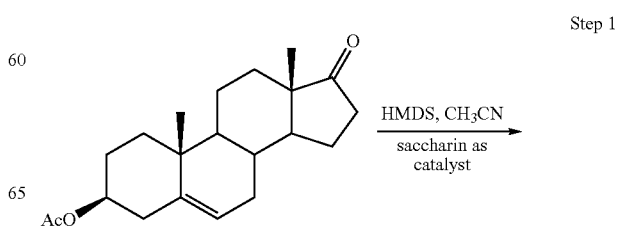

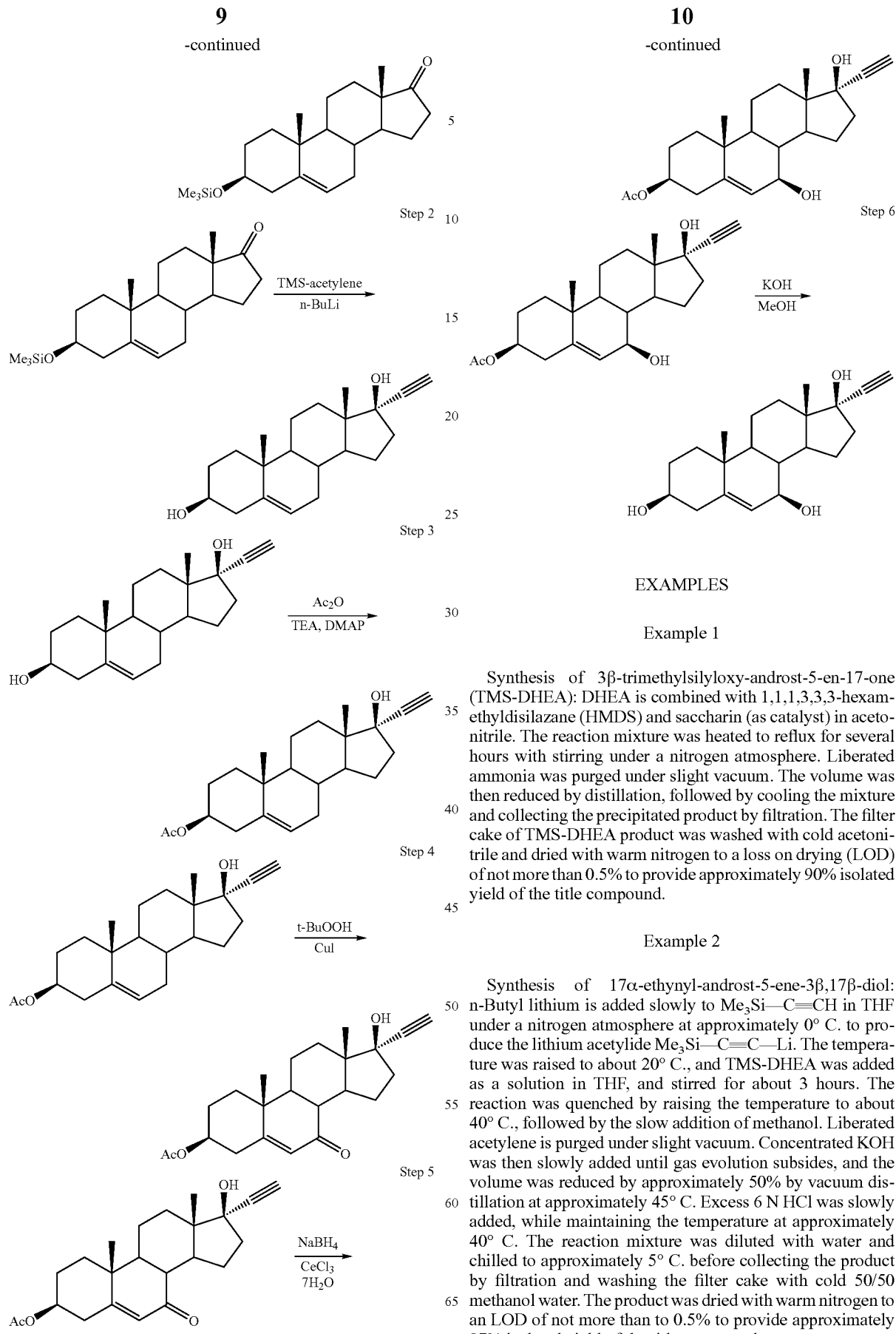

EXAMPLES

Example 1

Synthesis of 3β-trimethylsilyloxy-androst-5-en-17-one (TMS-DHEA): DHEA is combined with 1,1,1,3,3,3-hexamethyldisilazane (HMDS) and saccharin (as catalyst) in acetonitrile. The reaction mixture was heated to reflux for several hours with stirring under a nitrogen atmosphere. Liberated ammonia was purged under slight vacuum. The volume was then reduced by distillation, followed by cooling the mixture and collecting the precipitated product by filtration. The filter cake of TMS-DHEA product was washed with cold acetonitrile and dried with warm nitrogen to a loss on drying (LOD) of not more than 0.5% to provide approximately 90% isolated yield of the title compound.

Example 2

Synthesis of 17α-ethynyl-androst-5-ene-3β,17β-diol: n-Butyl lithium is added slowly to $Me_3Si-C\equiv CH$ in THF under a nitrogen atmosphere at approximately 0° C. to produce the lithium acetylide $Me_3Si-C\equiv C-Li$. The temperature was raised to about 20° C., and TMS-DHEA was added as a solution in THF, and stirred for about 3 hours. The reaction was quenched by raising the temperature to about 40° C., followed by the slow addition of methanol. Liberated acetylene is purged under slight vacuum. Concentrated KOH was then slowly added until gas evolution subsides, and the volume was reduced by approximately 50% by vacuum distillation at approximately 45° C. Excess 6 N HCl was slowly added, while maintaining the temperature at approximately 40° C. The reaction mixture was diluted with water and chilled to approximately 5° C. before collecting the product by filtration and washing the filter cake with cold 50/50 methanol water. The product was dried with warm nitrogen to an LOD of not more than to 0.5% to provide approximately 87% isolated yield of the title compound.

Example 3

Synthesis of 17α-ethynyl-3β-acetoxy-androst-5-en-17β-ol: 17α-ethynyl-androst-5-ene-3β,17β-diol was mixed with acetic anhydride, triethylamine, and a catalytic amount of DMAP in THF at refluxing temperature for at least 4 hours. The reaction progress was monitored by HPLC, and allowed to proceed until not more than 1% of the starting material remains. The mixture was then cooled to 30-50° C., and water was added, followed by cooling to approximately 0° C. for 1 hour. The crude product was collected by filtration, washed with cold acetonitrile, and dried with warm nitrogen to an LOD of not more than 5%. Crude product was characterized by HPLC and recrystallized from acetonitrile if the title compound was present in less than 95% peak area purity by HPLC. The recrystallized product was collected by filtration and dried to provide an overall isolated yield of 83% of the title compound.

Example 4

Synthesis of 17α-ethynyl-3β-acetoxy-17β-ol-androst-5-en-7-one: 17α-ethynyl-3β-acetoxy-androst-5-en-17β-ol was combined with t-butyl hydroperoxide and copper (I) iodide in acetonitrile and refluxed for two hours. The reaction was then quenched by cooling to about 50° C. followed by adding a large excess of aqueous sodium thiosulfate solution with stirring for at least 30 minutes. Under these conditions, organic and aqueous phases are not miscible. Agitation was halted to allow phase separation, and the aqueous phase (lower) is drained. The organic phase was extracted twice with aqueous sodium sulfite solution and brine by mixing at about 45° C. for at least 30 minutes, followed by phase separation, and removal of the aqueous phase. The resulting organic phase was concentrated to approximately 25% of the original volume by vacuum distillation at less than 45° C., and then chilled to about 5° C. The crude product, 17α-ethynyl-3β-acetoxyl-androst-5-en-7-one-17β-ol, was collected by filtration. The filtered cake was washed with cold acetonitrile/water and dried with warm nitrogen to an LOD of not more than 1.0%. The crude product was recrystallized twice by dissolving in N-methyl-pyrrolidinone (NMP) at approximately 90° C., followed by cooling to 0° C. for approximately one hour. The title compound was collected by filtration for an isolated overall yield of approximately 30%.

Example 5

Synthesis of 17α-ethynyl-androst-5-ene-3β,7β,17β-triol: 17α-ethynyl-3β-acetoxy-androst-5-en-7-one-17β-ol was reduced with NaBH$_4$ in THF/methanol in the presence of CeCl$_3$ at approximately 0° C. for about 2 hours. The reaction progress was monitored by HPLC. The reaction was quenched by slow addition of dilute HCl with liberated hydrogen removed under slight vacuum. Methyl tert-butyl ether (MTBE) was added and the reaction mixture washed twice with brine, discarding the aqueous phases. The 3β-acetoxy group from the crude product was removed by addition of methanolic KOH to the organic phase at approximately 0° C. for about 2 hours, with reaction progress monitored by HPLC. After completion, the reaction mixture was neutralized with acetic acid, and approximately one-half of the reaction volume was removed by vacuum distillation at less than 45° C. Approximately two-thirds of the original reaction mixture volume was added as isopropanol (IPA), and the volume was subsequently reduced to approximately one-fourth the original volume by vacuum distillation at less than 45° C. The residue mixture was cooled to 0° C., and the crude 17α-ethynyl-androst-5-ene-3β,7β,17β-triol was collected by filtration, washed with cold IPA, and dried with warm nitrogen.

Example 6

Recrystallization of 17α-ethynyl-androst-5-ene-3β,7β,17β-triol from Process A: Crude 17α-ethynyl-androst-5-ene-3β,7β,17β-triol from Example 5 was dissolved in refluxing methanol/water (~10/1). Methanol was removed by vacuum distillation while stirring, and replaced with sufficient water to maintain suspension of the crystallized product. The suspension is cooled to approximately 5° C. with stirring, and the product was recovered by filtration. The filtered cake was washed with water and dried under vacuum to less than 0.5% water to provide the title compound in approximately 69% isolated yield.

Scheme II: Process B, Route 1

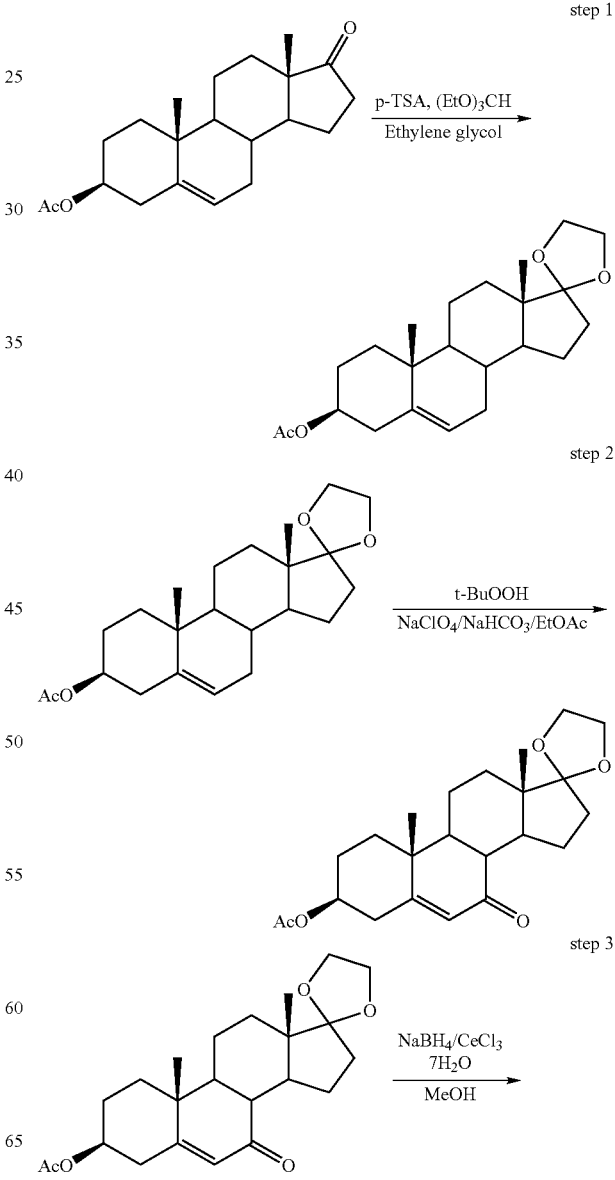

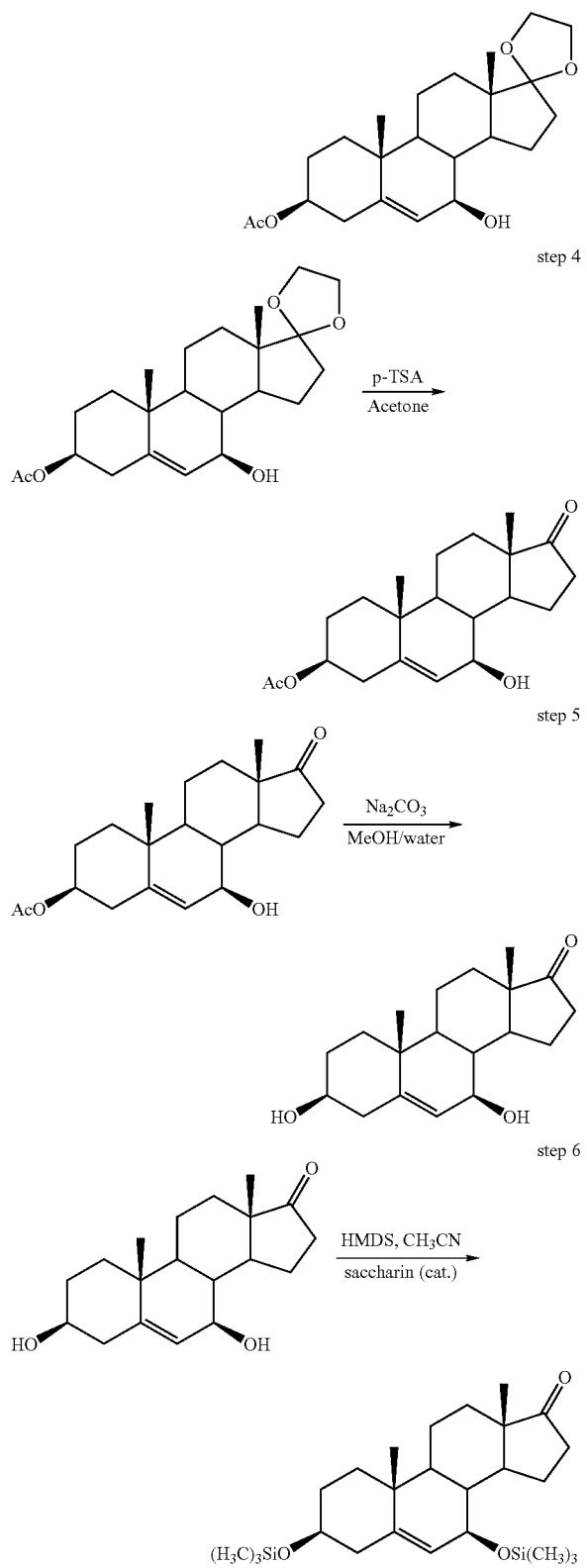

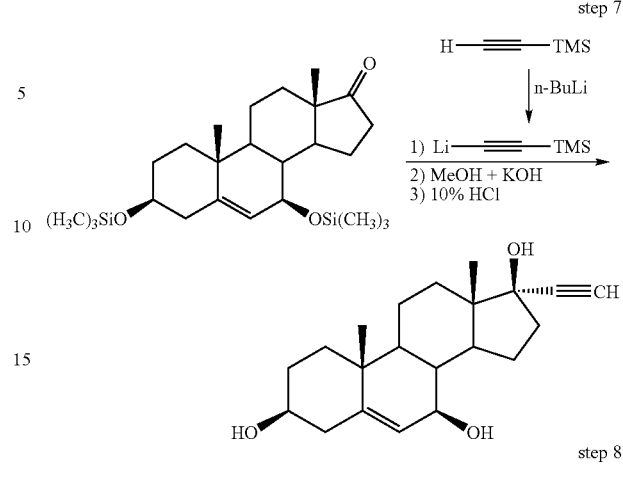

Example 7

Synthesis of 3β-acetoxy-androst-5-ene-17,17-ethylenedioxy: A 300 L reactor was charged with 36 kg of triethylorthoformate, 20 kg of 3β-acetoxy-5-androsten-17-one, 12.6 kg of ethylene glycol and 400 g of p-toluenesulfonic acid. The mixture was heated to reflux under nitrogen until the reaction was complete (about 2-3 hours). The mixture was then cooled to 60° C. and 16 kg of anhydrous ethanol and 400 ml of pyridine were added. The resulting solution was transferred to a container and refrigerated overnight. The solids that formed were filtered and washed with 80 kg of 50% ethanol and dried at 40-50° C. to afford 18.5-21.0 kg (81.5-92.5%) of the title compound.

Example 8

Synthesis of 3β-acetoxy-androst-5-en-7-one-17,17-ethylenedioxy: A 500 L reactor was charged with 200 kg ethyl acetate and 25 kg of 3β-acetoxy-androst-5-en-17,17-ethylenedioxy. The mixture was stirred for 30 minutes whereupon 55 kg of 70% t-butyl peroxide and 9 kg of sodium bicarbonate were added. The reaction mixture was then cooled to 0° C. and 116 kg of 13% sodium perchlorate (aq.) was added over 10 hours so that a reaction temperature below 5° C. and pH between 7.5 and 8.5 were maintained. After the reaction was complete, the organic layer was separated and the aqueous phase was extracted with ethyl acetate (35 kg×2). The combined organic phase was combined with a solution 33 kg of sodium sulfite in 167 kg of water, and the resulting mixture was stirred at 40° C. for 3 hours. The organic phase was washed with 50 kg of brine and concentrated to 55-60 kg whereupon 50 kg of methanol was added. After refrigeration overnight, a white solid was formed that was filtered and washed with 10 kg of methanol, and dried at 40-50° C. to yield 7.1-7.8 kg (27.4-30.1%) of the title compound.

Example 9

Synthesis of 3β-acetoxy-androst-5-ene-17,17-ethylenedioxy-7β-ol. A 500 L reactor was charged with 48 kg of THF, 10 kg of 3β-acetoxy-androst-5-en-7-one-17,17-ethylenedioxy and a solution of 9.6 kg $CeCl_3.7H_2O$ in 95 kg methanol. This mixture was cooled to 0° C. whereupon 2.0 kg of $NaBH_4$ was added in batches over 3 hours in order to maintain the temperature below 5° C. After stirring for 30 more minutes, 28 kg of acetone was added slowly in order to maintain the temperature below 5° C., with stirring continued for another 30 minutes. To the mixture was added 240 kg water with stirring continued for 1 hour. The organic solvents were removed under vacuum and the residue was extracted with ethyl acetate (100 kg+50 kg). The combined organic phase was washed with brine. Solvent was then removed to provide 8.6-8.9 kg (85.1-88.1%) of the title compound.

Example 10

Synthesis of 3β-acetoxy-androst-5-en-17-one-7β-ol: A 500 L reactor was charged with 315 kg of acetone and 18 kg of 3β-acetoxy-androst-5-en-17,17-ethylenedioxy-7β-ol. The mixture was cooled to 5° C. and 2.34 kg of p-toluenesulfonic acid was added slowly to maintain the temperature below 10° C. After stirring the mixture at 8-15° C. for 36-48 hours, 3.0 kg of sodium bicarbonate was added with stirring continued for 1 hour. Acetone was removed under vacuum, and to the residue was added 100 kg of water. The mixture was placed in a refrigerator overnight to give a white precipitate which was filtered to provide 33 kg (wet) of the title compound.

Example 11

Synthesis of androst-5-en-17-one-3β,7β-diol: A 500 L reactor was charged 230 kg methanol, 33 kg (wet) 3β-acetoxy-7β-hydroxy-5-androsten-17-one, 108 kg water and 15 kg $Na_2CO_3$. The mixture was heated to reflux for 3 hours. Methanol was removed under vacuum whereupon 250 kg of water was added to the residue. The mixture was put in refrigerator overnight to give a precipitate. The solids were collected by filtration, then washed with water and dried at 40-50° C. to yield 9.5-10.5 kg (67.9-75.0%) of the title compound as a white solid.

Example 12

Purification of androst-5-en-17-one-3β,7β-diol: A 500 L reactor was charged with 20 kg crude 3β,7β-dihydroxyandrost-5-en-17-one and 200 kg methanol and heated until all the solid dissolved. The solution was filtered while hot and after the filtrate cooled a white crystalline solid formed. The solids were collected by filtration, washed with small amount of methanol and dried at 40-50° C. The solid was then refluxed in 50 kg of ethyl acetate for 20 minutes. After cooling the solid was filtered and dried at 40-50° C. under vacuum to provide 15.2 kg (76%) of purified title compound.

Example 13

Synthesis of 3β,7β-bis-(trimethylsiloxy)-5-androsten-17-one: A mixture of 14.87 Kg of androst-5-en-17-one-3β,7β-diol, 23.8 Kg HMDS and 0.7 Kg saccharin catalyst in 100 L acetonitrile was heated to reflux for 8 hours with stirring under a nitrogen atmosphere. Liberated ammonia was purged under slight vacuum. The reaction volume was then reduced by distillation to collect 30 L of distillate (requires about 2 h). The reaction volume was further reduced to half of the original reaction volume by distillation under reduced pressure (700 mmHg), which requires about 2 h of heating at 50° C. The resulting uniform thick slurry is cooled to 5° C. (requires about 3 h), with additional acetonitrile added to maintain a minimum mixing volume, and held at that temperature for 1. The precipitated product was collected by filtration and dried at 45-50° C. under vacuum (29 mmHg) to a loss on drying (LOD) of not more than 1% (requires 20 h) to provide 16 Kg (81% yield) of the title compound (95% purity).

Example 14

Synthesis of 17α-ethynyl-5-androstene-3β,7β,17β-triol: To 11.02 Kg TMS-acetylene in 56.5 L tetrahydrofuran (THF) at −27° C. under a nitrogen atmosphere was added 8.51 L 10M n-BuLi. The n-butyl lithium was added very slowly to maintain a temperature at −7 to −27° C. (requires about 2 h) and the resulting reaction was stirred 10 min. at approximately 0° C. to produce TMS-lithium-acetylide. To the TMS-lithium-acetylide solution was added a solution of 25.41 Kg of 3β,7β-bis-(trimethylsiloxy)-5-androsten-17-one in 95.3 L THF filtered through a 25 µm filter while allowing the reaction temperature to rise to 20-25° C. After addition was completed, the reaction temperature was increased to 40-45° C. To quench the reactor contents, 31.8 L of methanol was added over a period of about 1 h followed by 3.81 Kg KOH in 18.4 L of water giving a final reactor temperature of 50° C. Liberated acetylene is purged under slight vacuum. The reactor contents were then concentrated by distillation at 80° C. for 1 h then under vacuum (175 mmHg) at about 70° C. (with an initial temperature of 25° C. to avoid bumping) to half of the original pot volume. The residue was cooled to about 10° C. and 35.0 Kg of deionized water was added, followed by 16.4 Kg 12N HCl while maintaining a pot temperature of about 10° C. and giving a final pH of 1. Additional 26.0 kg deionized water was added and the resulting mixture was stirred at about 5° C. for 1 h. The resulting slurry was filtered and washed with 75/25 mixture of methanol/water (16.9 L methanol, 5.6 L water). The collected solids were dried under vacuum (28 in Hg) at 45° C. for 12 h for a loss on drying of no more than 0.5% to provide 9.6 Kg of the title compound (83% yield).

Example 15

Recrystallization of 17α-ethynyl-5-androstene-3β,7β,17β-triol: Crude 9.6 Kg 17α-ethynyl-5-androstene-3β,7β,17β-triol prepared in Example 14 was dissolved in refluxing 50/50 methanol/water (4.2 Kg methanol and 5.4 Kg water). To the solution was added 33.4 Kg methanol followed by 37.6 Kg of THF. The mixture was heated to reflux and stirring was continued until all solids have dissolved, whereupon 99.8 Kg of deionized water was added while maintaining a reactor temperature of 60-75° C. The mixture was cooled to 0-5° C. over a period of 2 h and maintain at that temperature for 1 h while stirring was continued. The solids were recovered by filtration, washed with 9.6 Kg cold 50/50 methanol water and dried under vacuum (28 in Hg) at 50° C. for 8 h to provide 8.2 Kg of 17α-ethynyl-5-androstene-3β,7β,17β-triol. This first recrystallization is used to remove trace colored impurities from the initial product. A second recrystallization was conducted by heating the solid from the first recrystallization in ~10:1 methanol:water (145.8 Kg methanol and 18.2 Kg of water) to 80° C. until all the solids have dissolved. The solution at 55-60° C. was filtered through a 25 μm filter to remove particulate impurities, whereupon 2.5 Kg of methanol at 55-60° C. (used to rinse the reactor) was added. Vacuum distillation at 125 mmHg at 70° C. was conducted until 0.9 to 1.2 times the volume of methanol that was added to the reactor was collected as distillate with water added as necessary to permit stirring (about 120-160 Kg water added). Final reaction volume was 200-225 L. The reactor mixture was cooled to 0-5° C. and maintained at that temperature for 1 h. The resulting slurry was filtered and the filter cake rinsed with 10 Kg deionized water and dried under vacuum (28 in Hg) at 50° C. for 12 h to a residual water content of less than 0.5%. This isolation procedure was used to reduce the THF content in the final product. The yield was 8.0 Kg of recrystallized title compound (83% yield).

Scheme II: Process B, Route 2

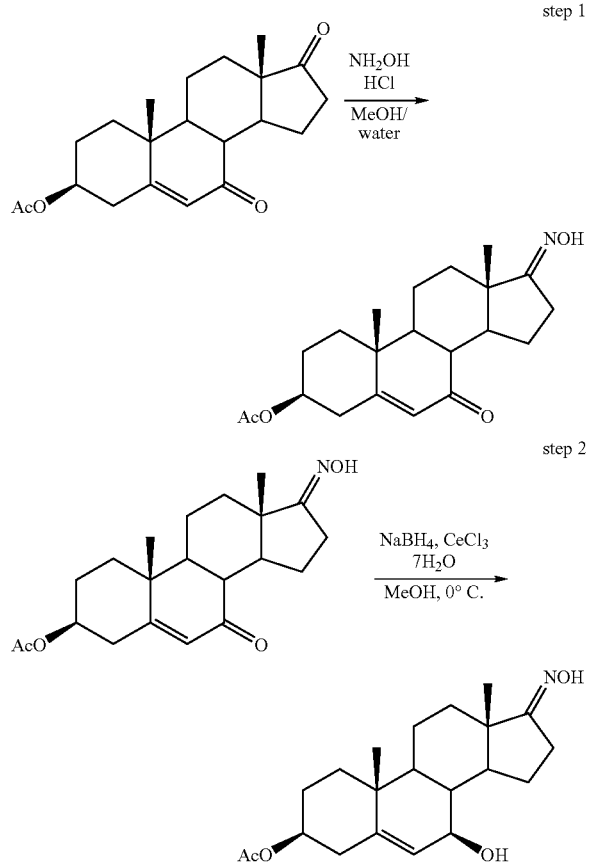

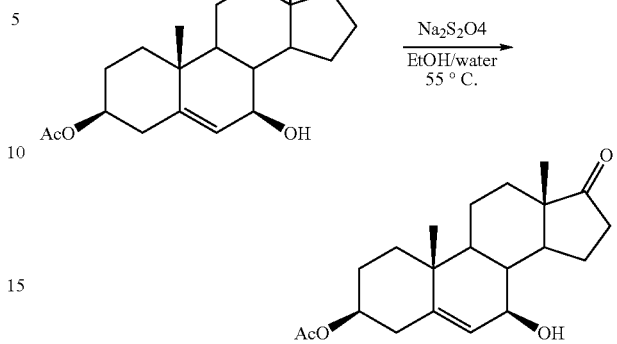

Example 16

Synthesis of 3β-acetoxy-androst-5-en-7-on-17-oxime: 3β-Acetoxy-androst-5-en-7,17-dione (45 g, 130 mmol) was dissolved in 800 mL methanol, 200 mL dichloromethane and 14.5 g Et$_3$N (144 mmol). To the solution at RT was added a solution of 10 g of hydroxylamine hydrochloride dissolved in 200 mL methanol. After stirring overnight, 200 mL of water was added followed by removal of volatile organics by evaporation under reduced pressure. To the resulting residue added an additional 1 L of water to give a while solid that was filtered and washed well with water. Obtained was 45 g of crude title oxime in 95% purity by $^1$H-NMR, which was used in the next step without further purification.

Example 17

Synthesis of 3β-acetoxy-androst-5-en-17-oxime-7β-ol: To a solution of 44 g of 3β-acetoxy-androst-5-en-7-on-17-oxime (100 mol %) in 800 mL methanol and 200 mL tetrahydrofuran was added 50 g of cerium chloride heptahydrate (110 mol %) in 20 mL of methanol. The resulting mixture was stirred until the solids were completely dissolved. To the solution cooled to about −5° C. was added 7 g sodium borohydride over 30 min. After stirring an additional 1.5 h at −5° C., the reaction mixture was quenched with acetone (100 mL) and then allowed to warm to room temperature over a 30 min. period. The quenched reaction mixture was concentrated under vacuum to remove volatile organics. To the residue was added 800 mL of water followed by extraction with ethyl acetate (3×500 mL). The combined organic extracts were washed with brine, dried over Na$_2$SO$_4$, then concentrated to provide 42 g of the title compound as a white foam, which was used in the next step without further purification.

Example 18

3β-acetoxy-androst-5-en-17-one-7β-ol: To a solution of 42 g of 3β-acetoxy-androst-5-en-17-oxime-7β-ol (100 mol %) in 200 mL of ethanol was added 100 mL of water followed by 80 g (400 mol %) of sodium dithionite. The reaction was heated at 55° C. and stirred 16 h. After cooling, the reaction was concentrated under reduced pressure. The residue was diluted with 100 mL of water, and the resulting solid was collected by filtration and redissolved in 1 L dichloromethane. To the DCM solution was added 1 g activated carbon. After stirring overnight the mixture was filtered, and the resulting filtrate was washed with water, dried and concentrated to provide 25 g of crude product. Recrystallization from ethyl acetate gave 22 g of the title compound.

Example 19

Estrogen receptor binding assay: A suitable example system is an estrogen receptor-kit manufactured by PanVera for ERβ, which contains recombinant estrogen receptor β ligand, FLUORMONE™ ES2 (ES2), a fluorescently labeled estrogen ligand, and appropriate buffer. The system was used in a fluorescence polarization competition assay in which a test article, such as a preparation of Compound 1 or a positive control displaces ES2 from its binding site. When bound to ERβ, ES2 tumbles slowly and has a high fluorescence polarization value. Unbound ES2 tumbles quickly and displays a low fluorescence polarization value. The change in polarization value in the presence of test compound then determines relative binding affinity of that test compound for ERR as expressed by its $IC_{50}$, which is the concentration of test compound that results in half-maximum shift in polarization. From $IC_{50}$, $K_i$ was calculated using the Cheng-Prusoff equation [*Biochem. Pharmacol.* 22: 3099-3108, (1973)]: $K_i = IC_{50}/(1+D/K_d)$ where D is the concentration of ES2 and $K_d$ is the dissociation constant for binding of ES2 to ERβ ($K_d = 4 \pm 2$ nM).

The competition assay was conducted according to the manufacturer's protocol (Lit. No. L0712, Rev. 10/03). Assay reagents used were bacculovirus expressed, full length human ERβ 4.5 pmol/μL in 50 mM Bis-Tris Propane (pH=9), 400 mM KCl, 2 mM DTT, 1 mM EDTA, 10% glycerol, ES2 400 nM in methanol and E2 screening buffer consisting of 100 mM potassium phosphate (pH=7.4), 100 μg/mL BGG, 0.02% $NaN_3$. The ES2-ERβ complex was formed with 20 μL 20 nM ERβ (0.020 pmol/μL) and 20 μL 2 nM ES2 (0.002 pmol/μL). Positive control (estrogen) solution was prepared using 20 μL of a 1.0 mM stock solution in DMSO and 80 μL DMSO. In a first dilution, 50 μL of this solution is added to 50 μL of DMSO, which is followed by dilutions in 2-fold increments, to provide for a 14 point dilution curve. In a second dilution, to 4 μL of each DMSO solution from the first dilution is added 400 μL of ES2 screening buffer. To 20 μL of test compound, serially diluted in the manner described immediately above, in a 384 well black flat bottom microtiter plate, was added 20 μL of the ES2-ERβ complex (0.5% final DMSO concentration) followed by incubation in the dark at 20-30° C. for 1-4 h. Test compound was treated similarly except the starting concentration was 10 mM. Fluorescence polarization values are obtained using 485 nm excitation and 530 nm emission interference filters. Binding assay for ERα was conducted as for ERβ except bacculovirus expressed, full length human 2.8 pmol/μL ERα was used as reagent with the ERα-ES2 complex formed from 20 μL 30 nM (0.030 pmol/μL) and 20 μL 2 nM ES2 (0.002 pmol/μL).

Example 20

AR, GR and PR receptor binding assays. The AR competition assay was conducted according to the manufacturer's protocol (Lit. No. L0844, Rev. 05/02) in the manner described for ERβ with the following exceptions. Reagents used were recombinant rat androgen receptor ligand binding domain tagged with His and GST [AR-LBD (His-GST)] 0.38 pmol/μL in buffer containing protein stabilizing agents and glycerol (pH=7.5), 200 nM FLUORMONE™ AL Green, which is a fluorescently labeled androgen ligand, in 20 mM Tris, 90% methanol and AR screening buffer containing stabilizing agents and glycerol (pH=7.5) with 2 μL of 1 mM DTT added per mL screening buffer (AR screening buffer 2 mM in added DTT) was used as the reagents. The AL Green-AR complex was formed with 20 μL 50 nM AR (0.050 pmol/μL) and 20 μL 2 nM AL Green (0.002 pmol/μL). $K_i$ was calculated using, for the dissociation constant for binding of the fluorophore to receptor, $K_d = 20 \pm 10$ nM.

The PR competition assay was conducted according to the manufacturer's protocol (Lit. No. L0503, Rev. 06/03) in the manner described for ERβ with the following exceptions. Reagents used were recombinant human progesterone receptor ligand binding domain tagged with GST [PR-LBD (GST)] 3.6 pmol/μL in 50 mM Tris (pH=8.0), 500 mM KCl, 1M urea, 5 mM DTT, 1 mM EDTA and 50% glycerol, 400 nM FLUORMONE™ PL Green, which is a fluorescently labeled progesterone ligand, in 20 mM Tris 90% methanol (pH=6.8) and PR screening buffer containing protein stabilizing agents and glycerol (pH=7.4) with 4 μL of 1 mM DTT added per mL screening buffer (PR screening buffer 4 mM in added DTT). The PL Green-PR complex was formed with 20 μL 80 nM PR (0.080 pmol/μL) and 20 μL 4 nM PL Green (0.004 pmol/μL). $K_i$ was calculated using, for the dissociation constant for binding of the fluorophore to receptor, $K_d = 40$ nM.

The GR competition assay was conducted according to the manufacturer's protocol (Lit. No. L0304, Rev. 12/01) in the manner described for ERβ with the following exceptions. Reagents used were recombinant full length human glucocorticoid receptor 0.240 pmol/μL in 10 mM phosphate buffer (pH=7.4), 200 mM $Na_2MoO_4$, 0.1 mM EDTA, 5 mM DTT and 10% glycerol, 200 nM FLUORMONE™ GS1, which is a fluorescently labeled glucocorticoid ligand, in 75% methanol, and GR screening buffer containing 100 mM potassium phosphate (pH=7.4), 200 mM $Na_2MoO_4$, 1 mM EDTA, 20% DMSO with 5 μL of 1 mM DTT per mL screening buffer added (GR screening buffer 5 mM in added DTT), 1 mM GR stabilizing peptide, which is a co-activator related peptide [see Chang, C. Y. *Mol. Cell. Biol.* 19: 8226-36 (1999)] in 10 mM phosphate buffer (pH=7.4) and 1 M DTT in water were used as the reagents. To 2.5 mL of the GR screening buffer is added 2.5 mL GR stabilizing peptide solution and 125 μL of 1 M DTT to form the GR stabilizing peptide-glucocorticoid receptor complex. Order of addition to the microtiter plate was 20 μL test compound in 1% DMSO, 10 μL of 16 nM GR (0.016 pmol/μL) and finally 10 μL of 4 nM GS1, followed by incubation in the dark at 20-30° C. for 4 h (total experiment time should not exceed 7 h). $K_i$ was calculated using, for the dissociation constant for binding of the fluorophore to receptor, $K_d = 0.3 \pm 0.1$ nM.

Example 21

Impurity profiling of 17α-ethynyl-5-androstene-3β,7β,17β-triol (Compound 1) preparations.

Process A: HPLC conditions for Impurity profiling of Compound 1 preparations form Process B are give in Table 1.

TABLE 1

| HPLC Conditions for Impurity Profiling of Compound 1 Preparations form Process A | |
|---|---|
| Column | Waters XTERA™ RP18, 3.5 μm, 4.6 mm (ID) × 150 mm (L) |
| Mobile Phase A | 100% Deionized water (degassed) |
| Mobile Phase B | 100% Acetonitrile (degassed) |
| Column Temperature | 30° C. |
| Detection Wavelength | 210 nm |
| Mobile Phase (initial) | 90% Mobile Phase A; 10% Mobile Phase B |

TABLE 1-continued

HPLC Conditions for Impurity Profiling of
Compound 1 Preparations form Process A

| Column | Waters XTERA™ RP18, 3.5 μm, 4.6 mm (ID) × 150 mm (L) | | | |
|---|---|---|---|---|
| Flow Rate (initial) | 1.0 mL/min | | | |
| Pump Gradient Program | Time (min) | % A | % B | Flow rate |
| | 0.00 | 90.0 | 10.0 | 1.00 |
| | 40.0 | 20.0 | 80.0 | 1.00 |
| | 43.00 | 20.0 | 80.0 | 1.00 |
| | 43.01 | 90.0 | 10.0 | 1.00 |
| | 50.00 (end) | 90.0 | 10.0 | 1.00 |
| Injection Volume | 10 μL | | | |
| Run Time | 50 minutes | | | |

TABLE 2

Impurities in example preparation of Compound 1 prepared according to Process A, Route 1 before recrystallization

| Compound | RRT* | Peak Area % |
|---|---|---|
| Unknown | 0.63 | 0.59 |
| Androst-5-en-17-one-3β,7β-diol | 0.87 | 0.12 |
| 17α-ethynyl-androst-5-ene-3β,7β,17β-triol (Compound 1) | 1.00 | 96.58 |
| 17α-ethynyl-androst-5-ene-3β,7α,17β-triol | 1.04 | 0.99 |
| 17α-ethenyl-androst-5-ene-3β,7β,17β-triol | 1.09 | 0.93 |
| 17α-ethynyl-androst-5-en-7-one-3β,17β-diol | 1.16 | 0.06 |
| Unknown | 1.47 | 0.04 |
| Unknown | 1.60 | 0.06 |
| 17α-ethynyl-androst-5-ene-3β,17β-diol | 1.75 | 0.63 |

*RRT-relative retention time (approximate) referenced to Compound 1 (i.e., RRT of Compound 1 arbitrarily set to 1.00)

TABLE 3

Impurities identified in example preparation of Compound 1 prepared according to Process A, Route 1 after recrystallization

| Compound | RRT* | Peak Area % |
|---|---|---|
| Unknown | 0.55 | 0.13 |
| Androst-5-ene-3β,7β,17β-triol | 0.87 | 0.06 |
| 17α-ethynyl-androst-5-ene-3β,7β,17β-triol (Compound 1) | 1.00 | 97.67 |
| 17α-ethynyl-androst-5-ene-3β,7α,17β-triol | 1.05 | 0.72 |
| 17α-ethenyl-androst-5-ene-3β,7β,17β-triol | 1.09 | 0.65 |
| 17α-ethynyl-androst-5-en-7-one-3β,17β-diol | 1.16 | 0.05 |
| Unknown | 1.60 | 0.05 |
| 17α-ethynyl-3β-acetoxy-androst-5-ene-17β-diol | 1.72 | 0.05** |
| 17α-ethynyl-androst-5-ene-3β,17β-diol | 1.75 | 0.61** |

*RRT-relative retention time (approximate) referenced to Compound 1 (i.e., RRT of Compound 1 arbitrarily set to 1.00)
**Impurities with determined binding capacity to estrogen receptors (either directly or from the product derived after ester hydrolysis)

Process B: HPLC conditions for Impurity profiling of Compound 1 preparations form Process B are identical to those of Table 1.

TABLE 4

Impurities identified in example preparation of Compound 1 prepared according to Process B, Route 1 before recrystallization

| Compound | RRT | Peak Area % |
|---|---|---|
| androst-5-en-17-one-3β,7β-diol | 0.94 | 0.80 |
| 17α-ethynyl-androst-5-ene-3β,7β,17β-triol (Compound 1) | 1.00 | 98.30 |
| 17α-ethynyl-androst-5-ene-3β,7α,17β-triol | 1.02 | 0.26 |
| 17α-ethynyl-androst-5-en-7-one-3β,17β-diol | 1.06 | 0.08 |

TABLE 4-continued

Impurities identified in example preparation of Compound 1 prepared according to Process B, Route 1 before recrystallization

| Compound | RRT | Peak Area % |
|---|---|---|
| 3β-acetoxy-androst-5-en-17-one-7β-ol | 1.24 | 0.10 |
| DHEA | 1.27 | 0.03 |
| 3β-acetoxy-androst-5-en-17-one | 1.46 | 0.09 |
| 3β-acetoxy-17-ethylenedioxy-androst-5-ene | 1.50 | 0.12 |
| 3β,7β-bis-(trimethsilyloxy)-androst-5-en-17-one | 1.68 | 0.21 |

*RRT-relative retention time (approximate) referenced to Compound 1 (i.e., RRT of Compound 1 arbitrarily set to 1.00)

What is claimed is:

1. A process for preparation of a 17α-alkynyl-androst-5-ene-3β, 7β, 17β-triol essentially free of steroid side-product(s) lacking an oxygen substituent at position 7 comprising the steps of
   (a) contacting a suitably protected dehydroepiandrosterone with an oxidizing agent to directly introduce a =O (ketone) functional group at position 7;
   (b) contacting a suitably protected androst-5-en-7,17-dione-3β-ol with a reducing agent to convert the =O (ketone) functional group at position 7 to hydroxyl predominantly in the β-configuration; and
   (c) contacting an optionally suitably protected alkynyl anion with suitably protected androst-5-en-17-one-3β, 7β-diol to introduce an alkynyl substituent at position 17 predominantly in the α-configuration by addition of the alkynyl anion to the =O (ketone) functional group at position 17
   wherein the 17α-alkynyl-androst-5-ene-3β, 7β,17β-triol obtained from step (c) is essentially free of binding activity at nuclear sex steroid receptors or is essentially free of an estrogenic 17α-alkynyl-androst-5-ene-3β, 17β-diol compound without purification to remove steroid side-product(s) lacking an oxygen substituent at position 7.

2. The process of claim 1 wherein the 17α-alkynyl-androst-5-ene-3β,7β,17β-triol is 17α-ethynyl-androst-5-ene-3β, 7β, 17β-triol.

3. The process of claim 1 wherein the suitably protected dehydroepiandrosterone has the structure of

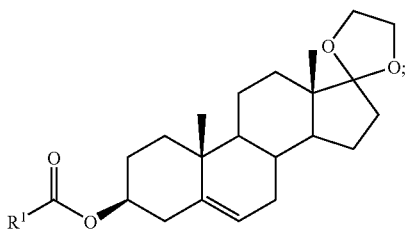

wherein $R^1$ is —H, $C_{1-6}$ alkyl, $C_{3-6}$ cycloalkyl, optionally substituted aryl or optionally substituted heteroaryl.

4. The process of claim 1 wherein the suitably protected androst-5-en-7,17-dione-3β-ol has the structure of

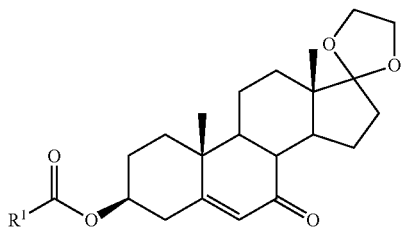

wherein R¹ is —H, $C_{1-6}$ alkyl, $C_{3-6}$ cycloalkyl, optionally substituted aryl or optionally substituted heteroaryl.

5. The process of claim 1 wherein the suitably protected androst-5-en-17-one-3β,7β-diol has the structure of

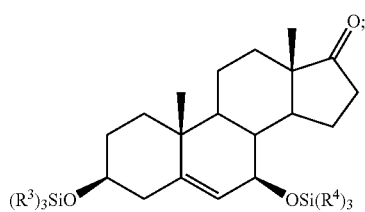

wherein each R³ and each R⁴ independently are $C_{1-6}$ alkyl or aryl.

6. The process of claim 5 wherein the suitably protected alkynyl anion has the structure of M—C≡C—Si(R⁵)₃ wherein R⁵ independently are $C_{1-6}$ alkyl or aryl and M is a Group I, Group II or transition metal.

7. The process of claim 6 wherein M is Li, Mg or Zn.

8. The process of any one of claims 3, 4 5 and 6 wherein R¹ is —CH₃, R³ and R⁴ is —CH₃ or R⁵ is CH₃.

9. A process for preparation of 17α-ethynyl-androst-5-ene-3β,7β,17β-triol essentially free of 17α-ethynyl-androst-5-ene-3β,17β-diol comprising the steps of
   (a) contacting suitably protected androst-5-en-7,17-dione-3β-ol having the structure of

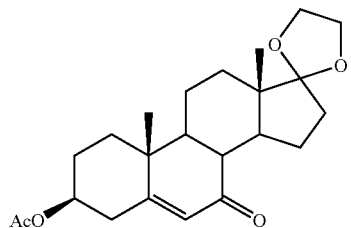

with a reducing agent to convert the ═O (ketone) functional group at position 7 to hydroxyl predominantly in the β-configuration;
   (b) converting the ketal functional group at position 17 in the product from step (a) to the ═O (ketone) functional group; and
   (c) converting the acetoxy group at position 3 to 3β-hydroxy or
   (b') converting the acetoxy group at position 3 in the product from step (a) to 3β-hydroxy; and
   (c') converting the ketal group at position 17 to the ═O (ketone) functional group; and
   (d) converting the hydroxyl groups at positions 3β and 7β in the product from steps (b) and (c) or steps (b') and (c') having the structure of

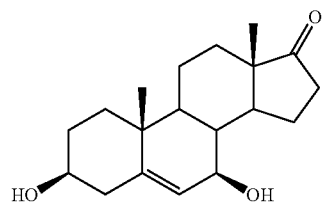

to Me₃SiO— groups; and
   (e) contacting the product from step (d) with lithium trimethylsilyl-acetylide to introduce an ethynyl substituent at position 17 predominately in the α-configuration by addition of the acetylide to the ═O (ketone) functional group at position 17;
   (f) contacting the reaction product from step (e) having the structure of

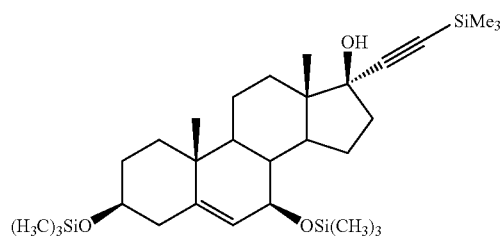

with an aqueous acid to replace —SiMe₃ with —H, whereby 17α-ethynyl-androst-5-ene-3β,7β,17β-triol is obtained essentially free of 17α-ethynyl-androst-5-ene-3β,17β-diol.

10. The process of claim 1 or 9 comprising the additional step of purifying 17α-alkynyl-androst-5-ene-3β,7β,17β-triol or 17α-ethynyl-androst-5-ene-3β,7β,17β-triol product by recrystallization.

11. The process of claim 10 wherein the 17α-alkynyl-androst-5-ene-3β,7β,17β-triol product is purified by recrystallization from methanol-water.

12. The process of claim 11 wherein the 17α-alkynyl-androst-5-ene-3β,7β,17β-triol is 17α-ethynyl-androst-5-ene-3β,7β,17β-triol.

* * * * *